US009606011B2

(12) United States Patent
Zapala

(10) Patent No.: US 9,606,011 B2
(45) Date of Patent: Mar. 28, 2017

(54) METHODS AND MATERIALS FOR CALIBRATING A CALORIC TEST

(75) Inventor: David A. Zapala, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 857 days.

(21) Appl. No.: 13/825,386

(22) PCT Filed: Sep. 20, 2011

(86) PCT No.: PCT/US2011/052285
§ 371 (c)(1),
(2), (4) Date: Mar. 21, 2013

(87) PCT Pub. No.: WO2012/040155
PCT Pub. Date: Mar. 29, 2012

(65) Prior Publication Data
US 2013/0184607 A1    Jul. 18, 2013

Related U.S. Application Data

(60) Provisional application No. 61/385,031, filed on Sep. 21, 2010.

(51) Int. Cl.
G01K 15/00 (2006.01)
G01J 5/00 (2006.01)
G01K 13/00 (2006.01)
G01K 19/00 (2006.01)
A61B 5/01 (2006.01)
A61B 5/00 (2006.01)

(52) U.S. Cl.
CPC ............. *G01K 19/00* (2013.01); *A61B 5/01* (2013.01); *A61B 5/4863* (2013.01); *A61B 5/6817* (2013.01)

(58) Field of Classification Search
USPC .............................................. 374/1, 121, 147
See application file for complete search history.

(56) References Cited

U.S. PATENT DOCUMENTS

| 4,106,493 | A | 8/1978 | Proctor et al. |
| 4,106,496 | A | 8/1978 | Proctor et al. |
| 4,244,377 | A | 1/1981 | Grams |
| 6,334,064 | B1 * | 12/2001 | Fiddian-Green ... A61B 5/14539 600/311 |
| 6,875,196 | B2 | 4/2005 | Abita et al. |

OTHER PUBLICATIONS

Anderson et al., "Caloric irrigators: air, open loop water and closed-loop water," British Journal of Audiology, vol. 29 (2), Apr. 1995, pp. 117-128.
Baloh et al., "Robert Bárány and the controversy surrounding his discovery of the caloric reaction." Neurology, vol. 58 (7), Apr. 2002, pp. 1094-1099.

(Continued)

*Primary Examiner* — Mirellys Jagan
(74) *Attorney, Agent, or Firm* — Fish & Richardson P.C.

(57) ABSTRACT

This document provides methods and materials for calibrating a caloric assay. For example, caloric calibration devices and methods for using caloric calibration devices to calibrate a caloric test are provided.

8 Claims, 3 Drawing Sheets

(56) References Cited

OTHER PUBLICATIONS

Burkard, "When standards and clinical practice collide," Acoustics Today, vol. 50(1), Apr. 2006, p. 1.

Capps et al., "Evaluation of the air caloric test as a routine Examination procedure," The Laryngoscope, vol. 83(7), Jul. 1973, pp. 1013-1021.

Coats et al., "The air caloric test. A parametric study," Archives of Otolaryngology, vol. 102(6), Jun. 1976, 343-354.

Ford et al., "Reliabilities of air and water caloric responses," Archives of Otolaryngology, vol. 104(7), Jul. 1978, pp. 380-382.

Greven, et al., "Caloric vestibular test with the use of air," The Annals of Otology, Rhinology, and Laryngology, vol. 88(1 Pt 1), Jan.-Feb. 1979, pp. 31-35.

International Preliminary Report on Patentability of international application No. PCT/US2011/052285, dated Apr. 4, 2013, 6 pp.

International Search Report and Written Opinion of international application No. PCT/US2011/052285, dated Apr. 18, 2012, 9 pp.

Maes et al., "Water irrigation versus air insufflation: A comparison of two caloric test protocols," International Journal of Audiology, vol. 46(5), May 2007, pp. 263-269.

Moon et al., "A comparison of test-retest variability of caloric induced nystagmus in a normal population using an air stimulus presented via a standard and modified irrigating probe," British Journal of Audiology, vol. 30(3), Jan. 1996, pp. 221-226.

Munro et al., The test-retest variability of the caloric test: a comparison of a modified air irrigation with the conventional water technique. British Journal of Audiology, vol. 30(5), Jan. 1996, pp. 303-306.

Press et al., "A study of five parameters of calorically-induced nystagmus in the clinical situation," The Journal of Auditory Research, vol. 19(2), Apr. 1979, pp. 127-135.

Torok, "Pitfalls in detecting vestibular decruitment with air calorics," ORL Journal for Oto-rhino-laryngology and its Related Specialties, vol. 41(3), Feb. 1979, pp. 143-146.

Westhofen et al., "Ballonmethode und Wasserspülung zur thermischen Vestibularisprüfung [Balloon method and water irrigation in thermal vestibular assessment. Electronystagmographic comparison of both methods]," Laryngologie, Rhinologie, Otologie, vol. 66(8), Aug. 1987, pp. 424-427 (English abstract only).

Zangemeister et al., "Air versus water caloric test," Clinical Otolaryngology Allied Science, vol. 5(6), Dec. 1980, pp. 379-387.

Zapala et al., "A comparison of water and air caloric responses and their ability to distinguish between patients with normal and impaired ears," Ear Hear, 29(4), 2008, pp. 585-600.

\* cited by examiner

METHODS AND MATERIALS FOR CALIBRATING A CALORIC TEST

CROSS-REFERENCE TO RELATED APPLICATIONS

This application is a National Stage application under 35 U.S.C. §371 of International Application No. PCT/US2011/052285, having an International Filing Date of Sep. 20, 2011, which claims the benefit of U.S. Provisional Application Serial No 61/385,031, filed Sep. 21, 2010. The disclosure of the prior application is considered part of (and is incorporated by reference in) the disclosure of this application.

BACKGROUND

1. Technical Field

This document relates to methods and materials for calibrating a caloric medium. For example, this document provides caloric calibration devices and methods for using caloric calibration devices to calibrate stimuli (e.g., a water or air medium) that can be used for a vestibular caloric test.

2. Background Information

The vestibular caloric test or caloric nystagmus test (e.g., a bilateral bithermal caloric nystagmus test or a monothermal caloric nystagmus test) is a test of the vestibulo-ocular reflex that generally involves measuring eye movements while irrigating cold or warm water or air into the external auditory canal. The test is commonly used by physicians, audiologists, and other trained professionals to validate a diagnosis of asymmetric function in the peripheral vestibular system.

SUMMARY

This document provides methods and materials for calibrating a caloric medium. For example, this document provides caloric calibration devices and methods for using caloric calibration devices to calibrate a caloric test stimulus. As described herein, a caloric calibration device provided herein can be used to determine a temperature change within a channel designed to resemble the ear canal of a human following introduction of an air or water caloric stimulus into the channel. This determined temperature change can be used to approximate the actual temperature change that occurs with a human test patient's ear canal when the same air or water caloric stimulus in delivered into the human test patient's ear canal, thereby calibrating the caloric test.

Since the devices provided herein provide a channel having dimensions that approximate the dimensions of a human ear canal, temperature changes induced by an air or water caloric stimulus at a measurement point of the caloric calibration device more realistically approximate actual temperature changes that occur in the ear canal, thereby making measurements more valid. In addition, the small size and standardized physical characteristics of a caloric calibration device provided herein can allow different clinics to reliably capture caloric temperatures, thereby removing one source of test variability across clinics. In some cases, a caloric calibration device provided herein can be used as a testing standard across one or more clinics or testing sites.

In general, one aspect of this document features a calibration device for calibrating a caloric medium. The device comprises, or consists essentially of, a housing defining a channel having a proximal end and a distal end, wherein the proximal end is open, wherein the distal end comprises a cap, wherein the length of the channel is between 15 mm and 200 mm, and wherein the diameter of the channel is between 3 mm and 12 mm. The housing can insulate the channel from temperature changes outside of the housing. The housing can comprise sponge material. The housing can comprise a metal or plastic material. The cap can be a membrane. The cap can comprise latex or rubber material. The cap can comprise piezoelectric crystal, glass, metal, a composite material, or a ceramic material. The channel can have a non-uniform diameter. The channel can bend to approximate the curves of an ear canal.

In another aspect, this document features a calibration device for calibrating a caloric medium. The device comprises, or consists essentially of, a housing and a tubular member defining a channel having a proximal end and a distal end, wherein the tubular member is at least partially located within the housing, wherein the proximal end is open, wherein the distal end comprises a cap, wherein the length of the channel is between 15 mm and 200 mm, and wherein the diameter of the channel is between 3 mm and 12 mm. The housing can insulate the channel from temperature changes outside of the housing. The housing can comprise sponge material. The housing can comprise a metal or plastic material. The tubular member can be positioned across the housing from one surface of the housing to an opposite surface of the housing. The tubular member can comprise a metal, plastic, or composite material. The cap can be a membrane. The cap can comprise latex or rubber material. The cap can comprise piezoelectric crystal, glass, metal, a composite material, or a ceramic material. The channel can have a non-uniform diameter. The channel can bend to approximate the curves of an ear canal.

In another aspect, this document features a kit for calibrating a caloric medium. The kit comprises, or consists essentially of, a calibration device and a temperature measurement instrument, wherein the calibration device comprises a housing defining a channel having a proximal end and a distal end, wherein the proximal end is open, wherein the distal end comprises a cap having an inner surface that faces towards the proximal end and an outer surface that faces away from the proximal end, wherein the length of the channel is between 15 mm and 200 mm, wherein the diameter of the channel is between 3 mm and 12 mm, wherein an air or water caloric stimulus is capable of being delivered into the channel from the proximal end, and wherein the temperature measurement instrument is adapted to measure a temperature change at the outer surface of the cap resulting from delivery of the air or water caloric stimulus into the channel. The housing can insulate the channel from temperature changes outside of the housing. The housing can comprise sponge material. The housing can comprise a metal or plastic material. The cap can be a membrane. The cap can comprise latex or rubber material. The cap can comprise piezoelectric crystal, glass, metal, a composite material, or a ceramic material. The channel can have a non-uniform diameter. The channel can bend to approximate the curves of an ear canal. The temperature measurement instrument can be an infrared thermometer. The kit can comprise a caloric irrigator configured to deliver the air or water caloric stimulus. The kit can comprise an ear speculum configured to assist delivery of the air or water caloric stimulus into the channel. The kit can comprise a caloric irrigator configured to deliver a water caloric stimulus. The kit can comprise a water basin configured to collect water discharged from the channel.

In another aspect, this document features a kit for calibrating a caloric medium. The kit comprises, or consists essentially of, a calibration device and a temperature measurement instrument, wherein the calibration device comprises a housing and a tubular member defining a channel having a proximal end and a distal end, wherein the tubular member is at least partially located within the housing, wherein the proximal end is open, wherein the distal end comprises a cap having an inner surface that faces towards the proximal end and an outer surface that faces away from the proximal end, wherein the length of the channel is between 15 mm and 200 mm, wherein the diameter of the channel is between 3 mm and 12 mm, wherein an air or water caloric stimulus is capable of being delivered into the channel from the proximal end, and wherein the temperature measurement instrument is adapted to measure a temperature change at the outer surface of the cap resulting from delivery of the air or water caloric stimulus into the channel. The housing can insulate the channel from temperature changes outside of the housing. The housing can comprise sponge material. The housing can comprise a metal or plastic material. The tubular member can be positioned across the housing from one surface of the housing to an opposite surface of the housing. The tubular member can comprise a metal, plastic, or composite material. The cap can be a membrane. The cap can comprise latex or rubber material. The cap can comprise piezoelectric crystal, glass, metal, a composite material, or a ceramic material. The channel can have a non-uniform diameter. The channel can bend to approximate the curves of an ear canal. The temperature measurement instrument can be an infrared thermometer. The kit can comprise a caloric irrigator configured to deliver the air or water caloric stimulus. The kit can comprise an ear speculum configured to assist delivery of the air or water caloric stimulus into the channel. The kit can comprise a caloric irrigator configured to deliver a water caloric stimulus. The kit can comprise a water basin configured to collect water discharged from the channel.

In another aspect, this document features a method of calibrating a caloric assay. The method comprises, or consists essentially of, (a) delivering an air or water caloric stimulus into a channel of a calibration device, wherein the channel comprises dimensions approximating those of a human ear canal, and wherein one end of the channel comprises a cap, and (b) measuring a temperature change at least a part of the cap resulting from delivery of the air or water caloric stimulus into the channel, wherein the temperature change provides an indication of the actual temperature change within a human ear canal when the air or water caloric stimulus is delivered to the human ear canal. In some cases, the calibration device can comprise a housing defining the channel, wherein the channel comprises a proximal end and a distal end, wherein the proximal end is open, wherein the distal end comprises the cap, wherein the length of the channel is between 15 mm and 200 mm, and wherein the diameter of the channel is between 3 mm and 12 mm. The housing can insulate the channel from temperature changes outside of the housing. The housing can comprise sponge material. The housing can comprise a metal or plastic material. The cap can be a membrane. The cap can comprise latex or rubber material. The cap can comprise piezoelectric crystal, glass, metal, a composite material, or a ceramic material. The channel can have a non-uniform diameter. The channel can bend to approximate the curves of an ear canal. In some cases, the calibration device can comprise a housing and a tubular member defining the channel, wherein the channel comprises a proximal end and a distal end, wherein the tubular member is at least partially located within the housing, wherein the proximal end is open, wherein the distal end comprises the cap, wherein the length of the channel is between 15 mm and 200 mm, and wherein the diameter of the channel is between 3 mm and 12 mm. The housing can insulate the channel from temperature changes outside of the housing. The housing can comprise sponge material. The housing can comprise a metal or plastic material. The tubular member can be positioned across the housing from one surface of the housing to an opposite surface of the housing. The tubular member can comprise a metal, plastic, or composite material. An infrared thermometer can be used to measure the temperature change. A caloric irrigator can be used to deliver the air or water caloric stimulus into the channel. An ear speculum can be used to assist delivery of the air or water caloric stimulus into the channel. A water basin can be used to collect water discharged from the channel.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials related to calibrating a caloric assay. For example, this document provides caloric calibration devices and methods for using caloric calibration devices to calibrate an air or water medium for use as a stimulus for a bilateral, bithermal caloric test or a monothermal caloric test. A caloric calibration device provided herein can include a channel having dimensions that approximate the dimensions of a human's ear canal. For example, a caloric calibration device provided herein can have a channel with a length between 10 mm and 40 mm (e.g., between 10 mm and 35 mm, between 10 mm and 30 mm, between 15 mm and 40 mm, between, 15 mm and 35 mm, or between 15 mm and 30 mm) and a diameter between 2 mm and 20 mm (e.g., between 2 mm and 15 mm, between 2 mm and 10 mm, between 3 mm and 20 mm, between, 3 mm and 15 mm, or between 3 mm and 12 mm) The channel can include a proximal end and a distal end. In some cases, the proximal end of the channel can be open, and a caloric stimulus (e.g., an air or water caloric stimulus) can be delivered into the channel via the proximal end. In some cases, the distal end can be open, and a temperature measurement instrument (e.g., a thermometer) can be configured to measure a temperature change at or near the distal end. In some cases, the distal end can be configured to include a cap. In such cases, a temperature measurement instrument (e.g., a thermometer such as an infrared thermometer) can be configured to measure a temperature change at or near the cap.

The methods and materials provided herein can be used by any appropriate person or patient. For example, a clinician or medical technician can use a caloric calibration device provided herein.

Figure 1:
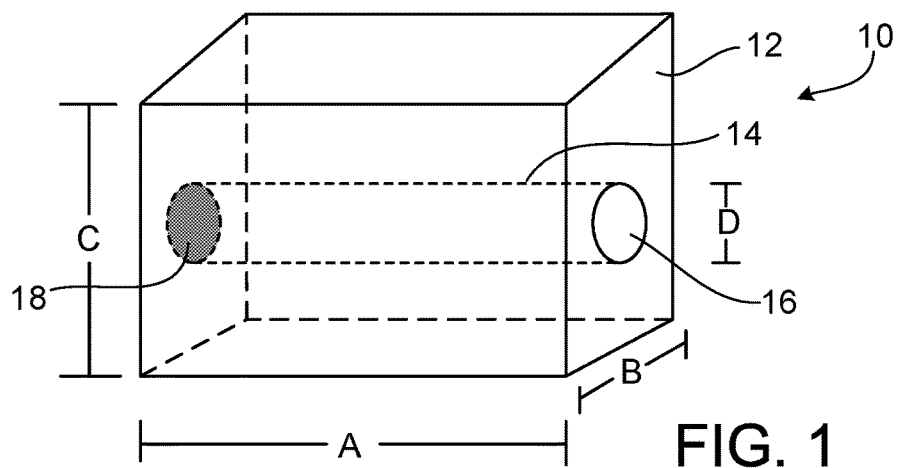
FIG. 1 is a side view of an exemplary embodiment of a caloric calibration device.

With reference to FIG. 1, caloric calibration device 10 can be configured to include a housing 12 defining a channel 14. Housing 12 can be configured to insulate channel 14 from temperature changes originating from outside channel 14. For example, housing 12 can be configured to insulate channel 14 from temperature changes that can occur when a medical technician holds caloric calibration device 10 with his or her fingers. Any appropriate material can be used to make housing 12. For example, housing 12 can be constructed from a sponge material, a metal material, a plastic material, or a composite material. Other examples of materials that can be used to make housing 12 include, without limitation, ceramics, rubbers, and various fluid or gel filled cavities.

Any appropriate dimensions of housing 12 can be used. For example, housing 12 can have a length (identified as "A" in FIG. 1) between 15 mm and 200 mm (e.g., between 20 mm and 200 mm, between 30 mm and 200 mm, between 40 mm and 200 mm, between 20 mm and 150 mm, between 20 mm and 100 mm, between 20 mm and 75 mm, and between 30 mm and 50 mm), a width (identified as "B" in FIG. 1) between 15 mm and 200 mm (e.g., between 20 mm and 200 mm, between 30 mm and 200 mm, between 40 mm and 200 mm, between 20 mm and 150 mm, between 20 mm and 100 mm, between 20 mm and 75 mm, and between 30 mm and 50 mm), and a height (identified as "C" in FIG. 1) between 15 mm and 200 mm (e.g., between 20 mm and 200 mm, between 30 mm and 200 mm, between 40 mm and 200 mm, between 20 mm and 150 mm, between 20 mm and 100 mm, between 20 mm and 75 mm, and between 30 mm and 50 mm) In addition, channel 14 can have any appropriate dimensions. For example, channel 14 can have a length (identified as "A" in FIG. 1) between 10 mm and 40 mm (e.g., between 10 mm and 35 mm, between 10 mm and 30 mm, between 10 mm and 25 mm, between 15 mm and 40 mm, between 20 mm and 40 mm, and between 15 mm and 30 mm) and a diameter (identified as "D" in FIG. 1) between 2 mm and 20 mm (e.g., between 2 mm and 15 mm, between 2 mm and 10 mm, between 3 mm and 20 mm, between, 3 mm and 15 mm, or between 3 mm and 12 mm) Housing 12 and channel 14 can have the same length or different lengths. For example, housing 12 can have a length that is longer or shorter than the length of channel 14. In some cases, channel 14 can have a non-uniform diameter and bend to approximate the curves of an ear canal.

In some cases, housing 12 can define channel 14 in that channel 14 is a channel formed in the material of housing 12. In some cases, housing 12 can define channel 14 in that a separate tubular member is inserted into housing 12. In such cases, the housing and tubular member can be constructed of the same or different material. In some cases, a tubular member can be constructed from a metal, a plastic, or a composite material. Other examples of materials that can be used to make a tubular member include, without limitation, piezoelectric crystal, rubber, or ceramic materials.

Figure 3:
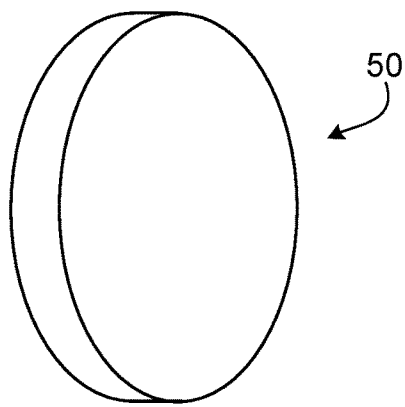
FIG. 3 is a side view of an exemplary cap for a caloric calibration device.

In some cases, channel 14 can have a proximal end 16 and a distal end 18. Proximal end 16 can be open such that a caloric stimulus (e.g., an air or water caloric stimulus) can be delivered into channel 14. Distal end 18 can be open or closed. For example, distal end 18 can include a cap as shown in FIG. 1. Such a cap can be constructed from any appropriate material including, without limitation, latex, rubber, piezoelectric crystal, glass, metal materials, composite materials, and ceramic materials. In some cases, a cap can be a membrane or can have a disc or puck configuration. For example, with reference to FIG. 3, cap 50 can be puck shaped. In some cases, a cap can be a fluid filled cap. For example, a cap can be a hermetically-sealed cap that contains water, saline, gelatin, or other material of caloric capacity.

Figure 2:
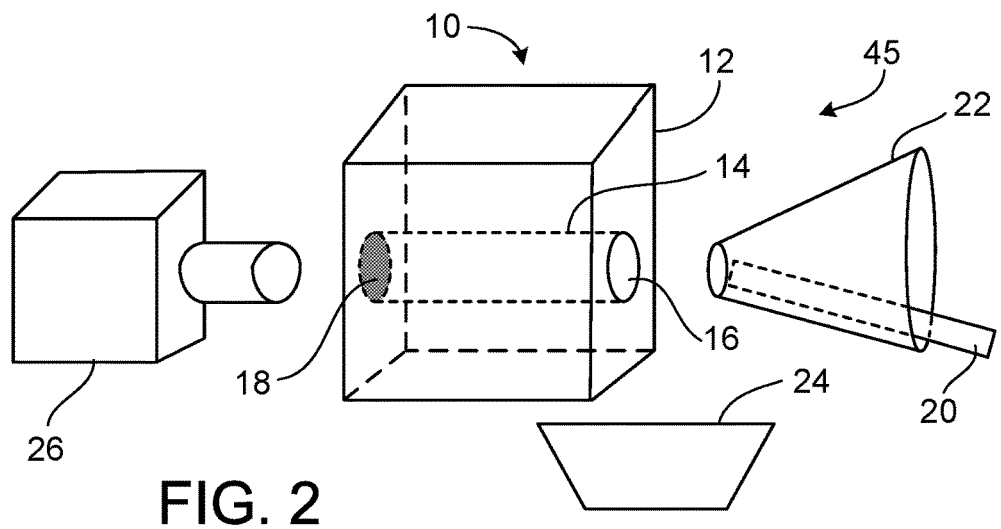
FIG. 2 is a side view of an exemplary embodiment of a kit containing an exemplary caloric calibration device.

With reference to FIG. 2, a kit 45 can include caloric calibration device 10 and optionally a caloric irrigator 20, an ear speculum 22, a water basin 24, a temperature measurement instrument 26, or any combination thereof. Caloric irrigator 20 can be configured to deliver an air or water caloric stimulus. For example, caloric irrigator 20 can be an Air Fx air caloric irrigator or an AquaStar water caloric irrigator commercially available from Micromedical Technologies, Inc. (Chatham, Ill.) or an ICS NCS-200 air caloric irrigator or an ICS NCI-480 water caloric irrigator available from GN Otometrics North America (Schaumburg, Ill.).

Ear speculum 22 can be a soft ear speculum. Ear speculums can be obtained commercially from Cardinal Health (Dublin, Ohio), Henry Schein Inc. (Melville, N.Y.), or McKesson Medical (San Francisco, Calif.). Water basin 24 can be any type of container configured to hold fluid. For example, water basin 24 can be a water basin obtained commercially from Novation (Irving, Tex.), Jansen Medical Supply, LLC (Houston Tex.), or Medline Industries, Inc. (Mundelein, Ill.). Temperature measurement instrument 26 can be any appropriate type of instrument capable of measuring temperature. Examples of temperature measurement instruments include, without limitation, mercury thermometers, piezoelectric thermometers, and infrared thermometers. Infrared thermometers can be obtained commercially from Ray-Tec Corporation (Santa Cruz, Calif.) or SPER Scientific (Scottsdale, Ariz.).

Figure 4:
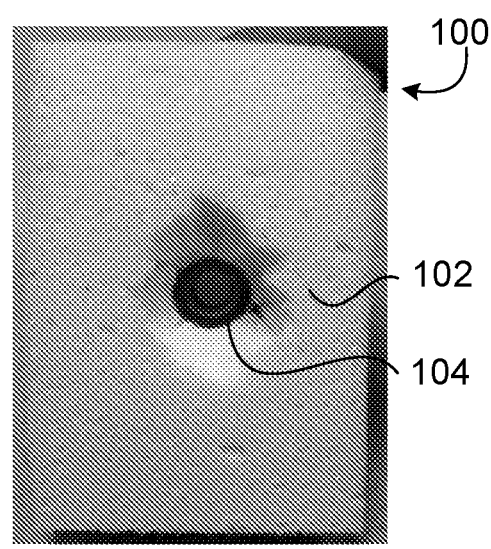
FIG. 4 is a photograph of one surface of an exemplary embodiment of a caloric calibration device.
Figure 5:
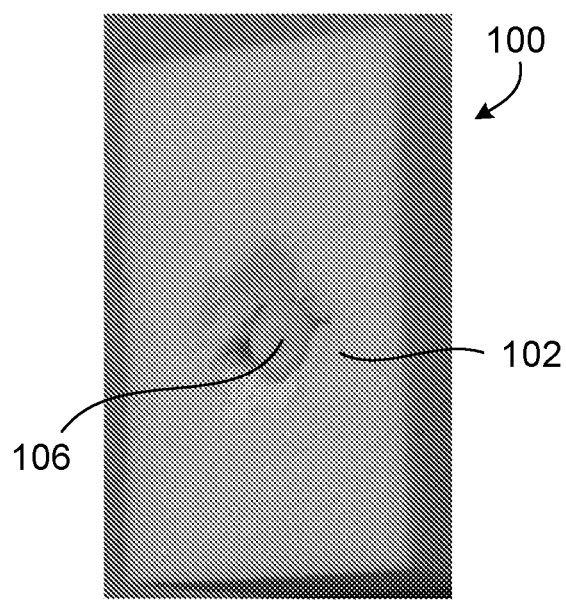
FIG. 5 is a photograph of an opposite surface of the caloric calibration device of FIG. 4.

With reference to FIGS. 4 and 5, caloric calibration device 100 can include a housing 102. Housing 102 can be a sponge material to provide insulation to a tubular member inserted into the sponge material. Proximal end 104 of the tubular member can be open as shown in FIG. 4, while distal end 106 can be closed via a cap (e.g., a membrane).

During use of a caloric calibration device provided herein or a kit provided herein, a caloric stimulus (e.g., an air or water caloric stimulus) can be delivered from caloric irrigator 20 into channel 14 such that air or water travels along the length of channel 14 toward distal end 18. Ear speculum 22 can be used to aid in the delivery of the caloric stimulus into channel 14. Temperature measurement instrument 26 (e.g., a thermometer or infrared thermometer) can be used to measure a change in temperature that occurs at a point or region at or near distal end 18 as a result of the caloric stimulus. For example, an infrared thermometer (e.g., Raynger MX infrared thermometer commercially available from Ray-Tec Corporation (Santa Cruz, Calif.)) can be used to measure a temperature change at an outer surface of a cap located at distal end 18. In some cases, a thermometer can be inserted into an open-ended distal end to measure a temperature change at the distal end. Water basin 24 can be used to collect any excess or discharged water, when a water caloric stimulus is used.

Once the measured temperature change is obtained, the same caloric stimulus can be applied to a human to be tested using a caloric test. The measured temperature change obtained using a caloric calibration device or kit provided herein can be used to provide an indication of the actual temperature change that occurs within the human's ear canal, thereby calibrating the measurements.

In some cases, if similar irrigation durations are used, a given clinic can use the measurement methods and devices described herein to set the temperature of their caloric medium to produce the same temperature in the test cavity that was used to generate a normal reference data set at a reference laboratory. This can result in the given clinic's caloric test performing in a statistically similar way to the reference laboratory and thus facilitate a valid use of the reference laboratory's normal reference values. Use of the methods and materials (e.g., devices) provided herein can facilitate the standardization of clinical caloric nystagmus tests.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for calibrating a caloric medium, wherein said kit comprises a calibration device and a temperature measurement instrument, wherein said calibration device comprises a housing defining a channel having a proximal end and a distal end, wherein said proximal end is open, wherein said distal end comprises a cap having an inner surface that faces towards said proximal end and an outer surface that faces away from said proximal end, wherein the length of said channel is between 15 mm and 200 mm, wherein the diameter of said channel is between 3 mm and 12 mm, wherein an air or water caloric stimulus is capable of being delivered into said channel from said proximal end, and wherein said temperature measurement instrument is adapted to measure a temperature change at said outer surface of said cap resulting from delivery of said air or water caloric stimulus into said channel.

2. The kit of claim 1, wherein said housing insulates said channel from temperature changes outside of said housing.

3. The kit of claim 1, wherein said cap is a membrane.

4. The kit of claim 1, wherein said cap comprises latex or rubber material.

5. The kit of claim 1, wherein said cap comprises piezo-electric crystal, glass, metal, a composite material, or a ceramic material.

6. The kit of claim 1, wherein said temperature measurement instrument is an infrared thermometer.

7. The kit of claim 1, wherein said kit comprises a caloric irrigator configured to deliver said air or water caloric stimulus.

8. The kit of claim 1, wherein said kit comprises an ear speculum configured to assist delivery of said air or water caloric stimulus into said channel.

* * * * *